(12) United States Patent
Wu et al.

(10) Patent No.: US 8,586,810 B2
(45) Date of Patent: Nov. 19, 2013

(54) CHIRAL DIENE LIGANDS, A FABRICATION METHOD THEREOF AND APPLICATIONS THEREOF

(75) Inventors: Hsyueh-Liang Wu, Taipei (TW); Chun-Chih Chen, Taipei (TW); Chia-Chen Liu, Taipei (TW); Wei-Ting Wei, Taipei (TW); Jo-Hsuan Fang, Taipei (TW)

(73) Assignee: National Taiwan Normal University, Taipei (TW)

( * ) Notice: Subject to any disclaimer, the term of this patent is extended or adjusted under 35 U.S.C. 154(b) by 0 days.

(21) Appl. No.: 13/608,222

(22) Filed: Sep. 10, 2012

(65) Prior Publication Data

US 2013/0096348 A1    Apr. 18, 2013

(30) Foreign Application Priority Data

Oct. 18, 2011    (TW) .............................. 100137782 A

(51) Int. Cl.
| | | |
|---|---|---|
| *C07C 1/00* | (2006.01) | |
| *C07C 205/00* | (2006.01) | |
| *C07C 13/465* | (2006.01) | |
| *C07C 19/08* | (2006.01) | |
| *C07C 17/00* | (2006.01) | |

(52) U.S. Cl.
USPC ........... 585/320; 570/130; 570/187; 568/941; 585/27

(58) Field of Classification Search
USPC .............. 570/130, 187; 568/941; 585/27, 320
See application file for complete search history.

(56) References Cited

PUBLICATIONS

Sumitomo Chemical Co. Ltd., Norbornadiene derivatives as energy converting agent, JP 57149251, Chemical Abstract, Mar. 1981.*
Wei-Ting Wei, et al., "Highly Enantioselective Rhodium-Catalyzed Asymmetric, 1,4-Addition Reactions of Arylboronic Acids to Acyclic α, β-Unsaturated Compounds: The Formal Synthesis of (−)-Indatraline", Chemistry—A European Journal, Aug. 31, 2011, pp. 11405-11409, vol. 17.

* cited by examiner

*Primary Examiner* — Jafar Parsa
(74) *Attorney, Agent, or Firm* — Muncy, Geissler, Olds & Lowe, PLLC

(57) ABSTRACT

The present invention proposes a chiral diene ligand, a fabrication method thereof and applications thereof. The chiral diene ligand is a bicyclo[2.2.1] diene ligand having structural specificity and high stability, which favors the bicyclo[2.2.1] diene ligand to take part in asymmetric transformations, particularly an asymmetric addition reaction involving a metal catalyst in a basic environment. Most of the products of the reactions implemented by the chiral diene ligands of the present invention have superior optical activity. The method of the present invention comprises a first oxidation step, a saponification step, a second oxidation step, a deprotonation step, and a cross-coupling step. The chiral diene ligand of the present invention is very suitable to be used in the fabrication or synthesis of various chemicals and medical products.

16 Claims, 2 Drawing Sheets

CHIRAL DIENE LIGANDS, A FABRICATION METHOD THEREOF AND APPLICATIONS THEREOF

BACKGROUND OF THE INVENTION

1. Field of the Invention

The present invention relates to chiral diene ligands, a fabrication method thereof and applications thereof, particularly to a set of bicyclo[2.2.1] chiral diene ligands, a fabrication method thereof, and applications thereof.

2. Description of the Related Art

In the nature, there are many molecules having chiral centers, wherein two molecules having an identical structural formula are mirror-symmetric to each other. A pair of chiral molecules have identical physical properties, such as the melting point, the boiling point and the spectral features, except the light polarization property.

In organisms, many amino acids and enzymes have chiral forms. Normally, a pair of mirror-symmetric isomers (enantiomers) cannot be simultaneously active to a biochemical reaction in an organism. Usually, one of enantiomers is allowed to take part in the reaction inside cells of an organism, but the other enantiomer may be harmful to the organism. For an example, the artificial sweetener D-Aspartame generates sweet taste, but the L-Aspartame generates bitter taste. For another example, the (S)-ethambutol can remedy pulmonary tuberculosis, but the (R)-ethambutol may blind human beings.

Therefore, many scholars are devoted to the development of preparing chiral molecules with high-enantioselectivity to function as intermediates for the syntheses of various biologically active compounds. A common measure thereof is to use a transition metal to catalyze the synthesis of chiral compounds. Normally, ligands with heteroatoms are good chiral modifiers to bind transition metals, forming asymmetric catalysts.

For many organometallic complexes, olefin is often used as the intermediary ligand because olefin has a weaker bonding to the transition metal and is likely to be replaced by heteroatom ligands in fabricating a chiral metal catalyst.

Hayashi, et al. had adopted norbornadiene as the material and used 9 reaction steps to synthesize a bicyclo[2.2.1]heptadiene ligand expressed by Structural Formula (I). The bicyclo[2.2.1]heptadiene ligand is efficacious in catalyzing asymmetric transformations. However, the fabrication thereof is too complicated.

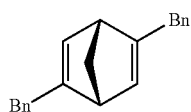

(I)

SUMMARY OF THE INVENTION

The present invention proposes a chiral diene ligand, a fabrication method thereof and applications thereof. The chiral diene ligands, bearing a bicyclo[2.2.1] skeleton, have structural specificity and high stability, and therefore favors the bicyclo[2.2.1] diene ligands to take part in asymmetric transformations. The fabrication process of the bicyclo[2.2.1] diene ligands is simpler than the conventional technology and has only 5 steps: a first oxidation step, a saponification step, a second oxidation step, a deprotonation step, and a cross-coupling step. The chiral diene ligands of the present invention can take part in a metal-catalyzed asymmetric addition reactions. Most products of the addition reactions catalyzed by the chiral diene ligands have a high optical purity (ee, enantiomeric excess). Therefore, the chiral diene ligands of the present invention are very suitable to be used in the fabrication or synthesis of various chemicals and biologically active products.

DETAILED DESCRIPTION OF THE INVENTION

Figure 1:
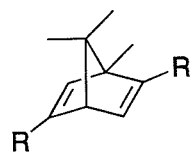
FIG. 1 shows the structural formula of a chiral diene ligand according to one embodiment of the present invention.
Figure 2:
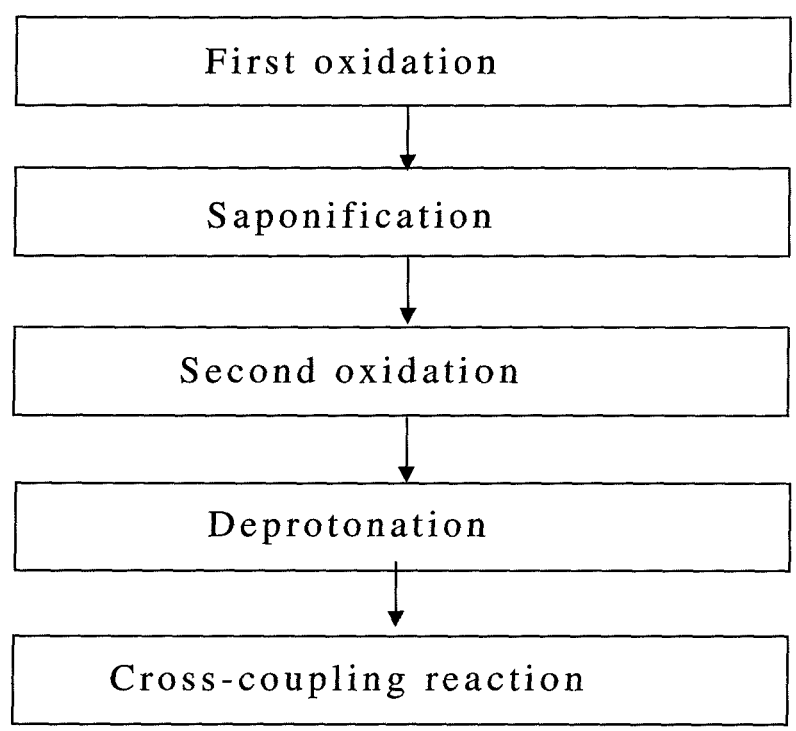
FIG. 2 shows a flowchart of a method for fabricating a chiral diene ligand according to one embodiment of the present invention.

Embodiment I: The Major Framwork of the Chiral Diene Ligands of the Present Invention Refer to FIG. 1. The chiral diene ligands of the present invention can be expressed by Structural Formula (II):

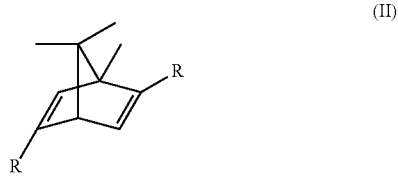

(II)

wherein R is a functional group selected from a group consisting of $C_6H_5$, 4-Me-$C_6H_4$, 4-Bu-$C_6H_4$, 4-Ph-$C_6H_4$, 1-nathphyl, 2-nathphyl, 4-F-$C_6H_4$, 4-Cl—$C_6H_4$, 4-$NO_2$—$C_6H_4$, alkenyl groups, alkynyl groups, and carbonyl groups.

Embodiment II: The Method for Fabricating the Chiral Diene Ligands of the Present Invention The method for fabricating the chiral diene ligands of the present invention comprises the following steps:

(1) a first oxidation step: undertaking an oxidation reaction of a cyclic reactant and chromium trioxide in an acidic environment to form a keto ester;

(2) a saponification step: undertaking a reaction of the keto ester and a basic material to form a saponified hydroxyl ketone;

(3) a second oxidation step: undertaking an oxidation reaction to convert the saponified hydroxyl ketone into a diketone;

(4) a deprotonation step: undertaking a reaction of the diketone, KHMDS (potassium hexamethyl disilazide) and the Comins' reagent to form bis-trifluoromethanesulfonate; and (5) a cross-coupling step: undertaking a cross-coupling reaction of the bis-trifluoromethanesulfonate in a basic environment.

In Step (1), the cyclic reactant is a derivative of bornyl esters. In one embodiment, the derivative of a bornyl ester is (1S)-(−)-bornyl acetate. The acidic environment is realized via filling an acid. In one embodiment, the acid is acetic acid. In another embodiment, the acid may be propanoic acid or butanoic acid. The reaction time is about 15-36 hours. In one embodiment, Step (1) yields a keto ester weighing about 30-34% of the weight of the cyclic reactant, and about 50 wt % of the cyclic reactant is recovered in Step (1). In Step (2), the basic material may be potassium hydroxide or sodium hydroxide. In one embodiment, ethyl alcohol is added into the saponification reaction.

In Step (3), an oxidizing agent, able to oxidize alcohols into ketones, is added to the second oxidation reaction. In one embodiment, the oxidizing agent is PCC (Pyridinium ChloroChromate). Step (3) yields a diketone weighing about 83% of the weight of the keto ester.

In Step (4), a base that deprotonates of the product of Step (3) is added in the deprotonation step; the subsequent addition of Comins' reagent gives the bis-triflate. In one embodiment, the base is KHMDS (Potassium HexaMethylDiSilazide). Step (4) yields a bis-triflate weighing about 91% of the weight of the diketone.

In Step (5), palladium catalyzes the cross-coupling reaction of the product of Step (4) and arylboronic acids in a basic environment. The basic environment is realized by potassium carbonate. The aryl functional group of the arylboronic acid is selected from a group consisting of $C_6H_5$, 4-Me-$C_6H_4$, 4-$^tBu$-$C_6H_4$, 4-Ph-$C_6H_4$, 1-nathphyl, 2-nathphyl, 4-F—$C_6H_4$, and 4-Cl—$C_6H_4$, 4-$NO_2$-$C_6H_4$, whereby can be formed various chiral diene ligands respectively containing different functional groups.

The yields of the chiral diene ligands fabricated according to the method of the present invention are listed in Table.1.

drofuran), $CH_2Cl_2$, toluene, $CH_3CN$, DMF (Dimethyl formamide). The basic liquid is a solution of potassium hydroxide. The yields of the products of the addition reactions and the enantioselectivities thereof are listed in Table.2. Table.2 shows that the chiral diene ligands of the present invention can catalyze the addition reaction of phenylboronic acid and cyclohexenone in several solvents under a basic environment. Most products of the addition reaction have high optical purity. In one embodiment, the catalyst has a catalytic loading of 3 mol %. In other embodiments, the concentration of the catalyst is modified to be 1 mol % or less.

TABLE 2 the yields and optical purities of the resulting 3-phenyl cyclohexanone of the addition reactions catalyzed by the chiral diene ligands of the present invention.

| Functional Group of Chiral Diene Ligand | Solvent | | | | | | | | | | | |
|---|---|---|---|---|---|---|---|---|---|---|---|---|
| | Dioxane | | THF | | $CH_2Cl_2$ | | Toluene | | $CH_3CN$ | | DMF | |
| | $Y^a$ | $OP^b$ | $Y^a$ | $OP^b$ | $Y^a$ | $OP^b$ | $Y^a$ | $OP^b$ | $Y^a$ | $OP^b$ | $Y^a$ | $OP^b$ |
| $C_6H_5$ | 94 | 91 | 67 | 93 | 12 | 95 | 12 | 97 | 20 | 96 | 40 | 89 |
| 4-Me—$C_6H_4$ | 91 | 92 | 65 | 95 | 11 | 96 | 14 | 98 | 12 | 98 | 42 | 92 |
| 4-$^tBu$—$C_6H_4$ | 86 | 64 | — | — | — | — | — | — | — | — | — | — |
| 4-Ph—$C_6H_4$ | 95 | 91 | 67 | 85 | 18 | 91 | 13 | 95 | 22 | 94 | 53 | 89 |
| 1-nathphyl | 88 | 83 | — | — | — | — | — | — | — | — | — | — |
| 2-nathphyl | 86 | 87 | — | — | — | — | — | — | — | — | — | — |
| 4-F—$C_6H_4$ | 92 | 93 | 73 | 88 | 13 | 89 | 6 | 79 | 57 | 94 | 77 | 94 |
| 4-Cl—$C_6H_4$ | 84 | 91 | 95 | 91 | 25 | 95 | 17 | 92 | 31 | 93 | 76 | 90 |
| 4-NO2—$C_6H_4$ | 89 | 92 | 72 | 87 | 6 | 93 | 15 | 93 | 39 | 94 | 54 | 91 |

$^a$Y denotes the yield of 3-phenyl cyclohexanone by %.
$^b$OP denotes the optical purity (ee value) of phenol cyclohexenone by %.

TABLE 1 the chiral diene ligands fabricated according to the method of the present invention and the yields thereof.

| Chiral Diene Ligand | Functional Group (R) | Yield |
|---|---|---|
| | $C_6H_5$ | 80% |
| | 4-Me—$C_6H_4$ | 58% |
| | 4-$^tBu$—$C_6H_4$ | 87% |
| | 4-Ph—$C_6H_4$ | 56% |
| | 1-nathphyl | 78% |
| | 2-nathphyl | 57% |
| | 4-F—$C_6H_4$ | 46% |
| | 4-Cl—$C_6H_4$ | 80% |
| | 4-NO2—$C_6H_4$ | 72% |

Embodiment III: The Result of the Addition Reaction of Phenylboronic Acid and Cyclohexenone, Which is Catalyzed by the Chiral Diene Ligands of the Present Invention The chiral diene ligand of the present invention catalyzes the addition reaction of phenylboronic acid and cyclohexenone to form 3-phenyl cyclohexanone according to Reaction Formula (A):

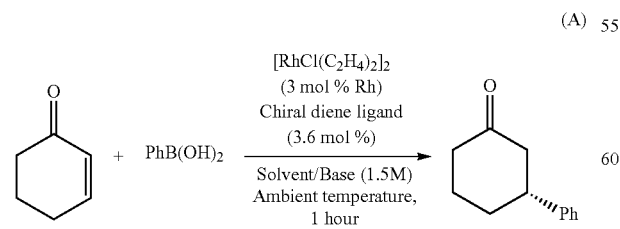

(A)

wherein the chiral diene ligand in Reaction Formula (A) contains a functional group selected from a group consisting of $C_6H_5$, 4-Me-$C_6H_4$, 4-$^tBu$-$C_6H_4$, 4-Ph-$C_6H_4$. The solvent is selected from a group consisting of dioxane, THF (tetrahy- Embodiment IV: The Influence of Solvents and Basic Liquids on the Addition Reactions of Phenylboronic Acid and Cyclohexenone, Which are Catalyzed by the Chiral Diene Ligands of the Present Invention This embodiment verifies the influence of solvents and basic liquids on the yield of the reaction. The results are listed in Table.3.

The influence of solvents: Most products of the reactions undertaken in ethers have excellent enantioselectivities (88-93%) and yields. The products of the reactions undertaken in alcohols also have fine activities and fine yields, especially in isopropyl alcohol (IPA).

The influence of basic liquids: It is observed from Table.3 that the type of the basic liquid has some influence on the yield and activity of the product while the solvent is the same. The product of the reaction in a solution of potassium hydroxide has higher yield and activity.

TABLE 3 the influence of solvents and basic liquids on the yields and optical purities of the resulting 3-phenyl cyclohexanone of the addition reactions of aphenylboronic acid and cyclohexenone, which are catalyzed by the chiral diene ligands of the present invention.

| Solvent | Basic Liquid | $Y^a$ | $OP^b$ |
|---|---|---|---|
| Dioxane | KOH | 92 | 93 |
| THF | KOH | 73 | 88 |
| Glyme | KOH | 64 | 91 |
| Methyl Alcohol | KOH | 100 | 92 |
| Ethyl Alcohol | KOH | 92 | 93 |
| IPA | KOH | 100 | 95 |
| IPA | LiOH | 100 | 93 |
| IPA | NaOH | 96 | 92 |
| IPA | SrOH | 88 | 94 |

TABLE 3-continued the influence of solvents and basic liquids on the yields and
optical purities of the resulting 3-phenyl cyclohexanone of the addition
reactions of aphenylboronic acid and cyclohexenone, which are catalyzed
by the chiral diene ligands of the present invention.

| Solvent | Basic Liquid | $Y^a$ | $OP^b$ |
|---------|--------------|-------|--------|
| IPA | KOH (IPA solution) | 96 | 94 |
| IPA | KOH (ethyl alcohol solution) | 97 | 96 |

$^a$Y denotes the yield of 3-phenyl cyclohexanone by %.
$^b$OP denotes the optical purity (ee value) of 3-phenyl cyclohexanone by %.

Embodiment V: The Influence of the Amount of the Catalyst on the Addition Reactions of Phenylboronic Acid and Cyclohexenone, Which are Catalyzed by the Chiral Diene Ligands of the Present Invention This embodiment adopts ethyl alcohol as the solvent and the ethyl alcohol solution of KOH as the basic liquid. The reactions are undertaken at a temperature of 30° C. for 1 hour to observe the influence of the catalytic loading of Rh. The results are listed in Table.4. It is found: the concentration of Rh does not affect the optical purity of the product. Even though the amount of Rh is as low as 0.05 mol %, the optical purity of the product does not vary obviously. The amount of Rh mainly affects the yield of the product.

TABLE 4 the influence of the amount of the catalyst on the yields and
optical purities of the resulting 3-phenyl cyclohexanone of the addition
reactions of phenylboronic acid and cyclohexenone, which are catalyzed
by the chiral diene ligands of the present invention.

| Catalyst (Rh) Loading (mol %) | $Y^a$ | $OP^b$ |
|---|---|---|
| 2.0 | 91 | 95 |
| 1.5 | 98 | 94 |
| 1.0 | 100 | 94 |
| 0.5 | 100 | 95 |
| 0.1 | 100[1] | 95 |
| 0.05 | 14[2] | 96 |

$^a$Y denotes the yield of 3-phenyl cyclohexanone by %.
$^b$OP denotes the optical purity (ee value) of 3-phenyl cyclohexanone by %.
[1] denotes that the reaction time is 8 hour.
[2] denotes that the reaction time is 24 hour.

Embodiment VI: The Influence of the Concentration of a Basic Liquid on the Addition Reactions of Phenylboronic Acid and Cyclohexenone, Which are Catalyzed by the Chiral Diene Ligands of the Present Invention This embodiment intends to promote the yield via decreasing the concentration of the liquid concentration in Reaction Formula (A). In this embodiment, the reaction in toluene is used to understand the influence of the concentration of the basic liquid on the yield of the product for an identical reaction time (24 hours). The reaction formula used in this embodiment is the same as Reaction Formula (A). The reactions are respectively undertaken in basic liquids of 0.6M and 1.5M KOH solutions. The yields and optical purities of the products of the reactions are listed in Table.5.

TABLE 5 the influence of the concentration of a basic liquid on the
yields and optical purities of the resulting 3-phenyl cyclohexanone of the
addition reactions of phenylboronic acid and cyclohexenone, which are
catalyzed by the chiral diene ligands of the present invention.

| Functional Group of Chiral Diene Ligand | Concentration of KOH | | | |
|---|---|---|---|---|
| | 1.5M | | 0.6M | |
| | $Y^a$ | $OP^b$ | $Y^a$ | $OP^b$ |
| $C_6H_5$ | 17 | 92 | 13 | 79 |
| 4-Me—$C_6H_4$ | 15 | 93 | 6.8 | 87 |
| 4-Ph—$C_6H_4$ | 25 | 90 | 14 | 68 |
| 4-F—$C_6H_4$ | 95 | 88 | 73 | 88 |
| 4-Cl—$C_6H_4$ | 34 | 91 | 34 | 85 |
| 4-NO2—$C_6H_4$ | 31 | 87 | 44 | 65 |

$^a$Y denotes the yield of 3-phenyl cyclohexanone by %.
$^b$OP denotes the optical purity (ee value) of 3-phenyl cyclohexanone by %.

Embodiment VII: Application of the Chiral Diene Ligands of the Present Invention to the Asymmetric Addition Reaction of Cyclic α,β-Unsaturated Carbonyl Compounds and Arylboronic Acids The chiral diene ligands of the present invention catalyze the addition reaction of cyclic α,β-unsaturated carbonyl compounds and arylboronic acids according to Reaction Formula (B):

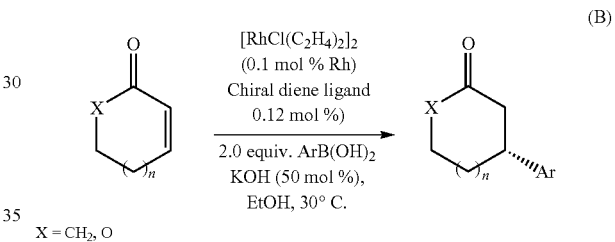

(B)

$X = CH_2, O$

TABLE 6 the yields and optical purities of the products of the addition
reactions of cyclic α,β-unsaturated carbonyl compounds and arylboronic
acids, which are catalyzed by the chiral diene ligands of the present
invention.

| X, n | Functional Group of Chiral Diene Ligand (Ar) | Reaction Time (hour) | $Y^a$ | $OP^b$ |
|---|---|---|---|---|
| $X = CH_2, n = 2^±$ | $C_6H_5$ | 8 | 93 | 95 |
| $X = CH_2, n = 2^±$ | 4-Ph—$C_6H_4$ | 9 | 90 | 98 |
| $X = CH_2, n = 2^±$ | 4-MeO—$C_6H_4$ | 1 | 85 | 94 |
| $X = CH_2, n = 2^±$ | 2-MeO—$C_6H_4$ | 1 | 95 | 92 |
| $X = CH_2, n = 2^±$ | 4-Me—$C_6H_4$ | 1 | 100 | 90 |
| $X = CH_2, n = 2^*$ | 2-Me—$C_6H_4$ | 1 | 96 | 90 |
| $X = CH_2, n = 2^*$ | 4-F—$C_6H_4$ | 1 | 100 | 96 |
| $X = CH_2, n = 2^*$ | 3-$CF_3$—$C_6H_4$ | 1 | 96 | 96 |
| $X = CH_2, n = 1^±$ | $C_6H_5$ | 2 | 99 | 96 |
| $X = CH_2, n = 1^±$ | 4-MeO—$C_6H_4$ | 1 | 98 | 92 |
| $X = CH_2, n = 1^*$ | 2-MeO—$C_6H_4$ | 1 | 93 | 95 |
| $X = CH_2, n = 1^*$ | 4-F—$C_6H_4$ | 1 | 99 | 96 |
| $X = CH_2, n = 2^*$ | $C_6H_5$ | 1.5 | 100 | 95 |
| $X = CH_2, n = 2^*$ | 4-Me—$C_6H_4$ | 1.5 | 100 | 89 |
| $X = O^*$ | $C_6H_5$ | 2(7) | 43(59)$^c$ | 95(97)$^c$ |
| $X = O^*$ | 4-Me—$C_6H_4$ | 2(7) | 38(54)$^c$ | 85(92)$^c$ |

$^±$The reaction scale is 6 mmol.
*The reaction scale is 12 mmol.
$^a$Y denotes the yield of the product of the addition reaction by %.
$^b$OP denotes the optical purity (ee value) of the product of the addition reaction by %.
$^c$the data in the parenthesis denotes the use of dioxane as a solvent.

From Table.6, it is known: when the reactant is 2-cyclohexenone (=$CH_2$, n=2) or 2-cyclopenten-one ((X=$CH_2$, n=1), the product has good yield and excellent enantioselectivity; when X=O, ring-opening occurs in the reaction and results in the decrease of yield and activity. However, the product of ring-opening is decreased when dioxane is used as the solvent.

In conclusion, the chiral diene ligands of the present invention have very high structural specificity and are very suitable to implement various asymmetric reactions. The fabrication method of the chiral diene ligands is simple and easy to operate. The chiral compounds implemented by the chiral diene ligands of the present invention have very high optical purity and are very suitable to function as the intermediates in the development, fabrication, or synthesis of various chemicals and drugs.

What is claimed is:

1. A chiral diene ligand, expressed by a structural formula:

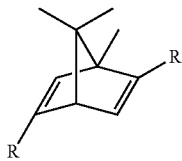

wherein R is a functional group selected from a group consisting of $C_6H_5$, 4-Me-$C_6H_4$, 4-Bu-$C_6H_4$, 4-Ph-$C_6H_4$, 1-nathphyl, 2-nathphyl, 4-F—$C_6H_4$, 4-Cl—$C_6H_4$, 4-$NO_2$—$C_6H_4$, alkenyl groups, alkynyl groups, and carbonyl groups.

2. A method for fabricating a chiral diene ligand, comprising

Step (1)—a first oxidation step: undertaking an oxidation reaction of a cyclic reactant and chromium trioxide in an acidic environment to form a keto ester;

Step (2)—a saponification step: undertaking a reaction of said keto ester and a basic material to form a saponified keto ester;

Step (3)—a second oxidation step: undertaking a reaction of said saponified keto ester and an oxidizing agent to form a dikentone;

Step (4)—a deprotonation step: undertaking a reaction of said dikentone, KHMDS (potassium hexamethyl disilazide) and a Comins' reagent to form trifluoromethanesulfonate; and Step (5)—a cross-coupling step: undertaking a cross-coupling reaction of said trifluoromethanesulfonate in a basic environment, wherein said chiral diene ligand is expressed by a structural formula:

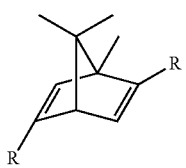

wherein R is a functional group selected from a group consisting of $C_6H_5$, 4-Me-$C_6H_4$, 4-Bu-$C_6H_4$, 4-Ph-$C_6H_4$, 1-nathphyl, 2-nathphyl, 4-F—$C_6H_4$, 4-Cl—$C_6H_4$, 4-$NO_2$—$C_6H_4$, alkenyl groups, alkynyl groups, and carbonyl groups.

3. The method for fabricating a chiral diene ligand according to claim 2, wherein said cyclic reactant in said Step (1) is a derivative of a bornyl ester.

4. The method for fabricating a chiral diene ligand according to claim 3, wherein said acidic environment in said Step (1) is an acid, and wherein said acid is selected from a group consisting of acetic acid, propanoic acid and butanoic acid.

5. The method for fabricating a chiral diene ligand according to claim 4, wherein said basic material in said Step (2) is potassim hydroxide or sodium hydroxide.

6. The method for fabricating a chiral diene ligand according to claim 5, wherein ethyl alcohol is added to said reaction in said Step (2).

7. The method for fabricating a chiral diene ligand according to claim 5, wherein said basic environment in said Step (5) is via adding potassium carbonate.

8. The method for fabricating a chiral diene ligand according to claim 6, wherein said basic environment in said Step (5) is via adding potassium carbonate.

9. The method for fabricating a chiral diene ligand according to claim 7, wherein said oxidizing agent oxidizes alcohols into ketones.

10. The method for fabricating a chiral diene ligand according to claim 8, wherein said oxidizing agent oxidizes alcohols into ketones.

11. The method for fabricating a chiral diene ligand according to claim 9, wherein palladium is used as a catalyst in said Step (5).

12. The method for fabricating a chiral diene ligand according to claim 10, wherein palladium is used as a catalyst in said Step (5).

13. A method for applying a chiral diene ligand, for said chiral diene ligand to take part in an asymmetric addition reaction involving a metal catalyst, wherein said chiral diene ligand is expressed by a structural formula:

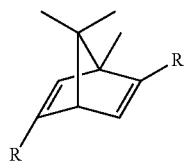

wherein R is a functional group selected from a group consisting of $C_6H_5$, 4-Me-$C_6H_4$, 4-Bu-$C_6H_4$, 4-Ph-$C_6H_4$, 1-nathphyl, 2-nathphyl, 4-F—$C_6H_4$, 4-Cl—$C_6H_4$, 4-$NO_2$—$C_6H_4$, alkenyl groups, and alkynyl groups.

14. The method for applying a chiral diene ligand accordign to claim 13, wherein said metal catalyst is rhodium.

15. The method for applying a chiral diene ligand accordign to claim 14, wherein a solvent is added to said addition reaction, and wherein said solvent is selected from a group consisting of dioxane, THF (tetrahydrofuran), $CH_2Cl_2$, toluene, $CH_3CN$, DMF (Dimethyl formamide).

16. The method for applying a chiral diene ligand accordign to claim 15, wherein said addition reaction is undertaken in a basic environment.

* * * * *